US008162906B2

(12) United States Patent
Terrill et al.

(10) Patent No.: US 8,162,906 B2
(45) Date of Patent: Apr. 24, 2012

(54) MEDICAL DEVICE FOR DELIVERY OF LIQUIDS

(76) Inventors: Matthew J. Terrill, Costa Mesa, CA (US); David E. Louvet, Costa Mesa, CA (US)

( * ) Notice: Subject to any disclaimer, the term of this patent is extended or adjusted under 35 U.S.C. 154(b) by 0 days.

(21) Appl. No.: 12/777,078

(22) Filed: May 10, 2010

(65) Prior Publication Data

US 2010/0286659 A1 Nov. 11, 2010

Related U.S. Application Data

(63) Continuation-in-part of application No. 11/639,980, filed on Dec. 15, 2006, now abandoned.

(60) Provisional application No. 60/750,884, filed on Dec. 16, 2005, provisional application No. 61/176,863, filed on May 8, 2009.

(51) Int. Cl.
*A61M 35/00* (2006.01)
*A61M 31/00* (2006.01)

(52) U.S. Cl. ........ 604/311; 604/181; 604/187; 604/218; 604/275

(58) Field of Classification Search .................. 604/116, 604/181, 187, 239, 264, 311, 218, 275, 310
See application file for complete search history.

(56) References Cited

U.S. PATENT DOCUMENTS

| | | | | |
|---|---|---|---|---|
| 4,769,011 | A * | 9/1988 | Swaniger | 604/218 |
| 5,899,692 | A * | 5/1999 | Davis et al. | 433/80 |
| 6,569,089 | B1 * | 5/2003 | Covington et al. | 600/199 |
| 2002/0108614 | A1 * | 8/2002 | Schultz | 128/207.14 |
| 2005/0004519 | A1 * | 1/2005 | Van Jaarsveldt | 604/117 |
| 2006/0161117 | A1 * | 7/2006 | Young | 604/264 |

* cited by examiner

*Primary Examiner* — Nicholas Lucchesi
*Assistant Examiner* — Leah Stohr
(74) *Attorney, Agent, or Firm* — Gates & Cooper LLP

(57) ABSTRACT

An apparatus and method for delivering liquid within an orifice of an animal is disclosed. In an exemplary embodiment, the apparatus comprises a hollow syringe defining a vessel having an open end; a plunger, slidingly and sealingly disposed within the vessel; and a flexible delivery tube, having a first end sealingly coupled to the open end and a delivery end for dispensing the liquid proximate the orifice. A light source directing light to the delivery end of the flexible tube may also be included.

17 Claims, 9 Drawing Sheets

MEDICAL DEVICE FOR DELIVERY OF LIQUIDS

CROSS-REFERENCE TO RELATED APPLICATIONS

This application is a continuation in part of U.S. patent application Ser. No. 11/639,980, entitled "MEDICAL DEVICE FOR DELIVERY OF LIQUIDS," by Matthew J. Terrill, filed Dec. 15, 2006, which claims benefit of U.S. Provisional Patent Application No. 60/750,884, entitled "MEDICAL TOOL FOR ANIMAL EARS," by Matthew J. Terrill, filed Dec. 16, 2005, both of which applications are hereby incorporated by reference herein.

This application also claims benefit of U.S. Provisional Patent Application No. 61/176,863, entitled "MEDICAL TOOL," by Matthew J. Terrill and David E. Louvet, filed May 8, 2009, which application is also hereby incorporated by reference herein.

BACKGROUND OF THE INVENTION

1. Field of the Invention

This invention relates generally to systems and methods for dispensing medication and specifically to a method and apparatus for dispensing medication and other liquids in the ear, nose and throat of animals and human beings.

2. Description of the Related Art

FIG. 1 is a diagram showing hearing structures 100 of a canine. The structures 100 include the pinna 102 or outer ear, an opening to the ear canal 104, and the inner ear, which comprises the ear canal 106 and the middle ear cavity 108. The ear canal 106 includes a vertical ear canal 106A and a horizontal ear canal 106B. The vast majority of ear infections in canines begins and ends in the lower portion 110 of the vertical ear canal 106A. The current method for applying liquid medicine into the ear of any domesticated animals has no tool specifically designed to get medicine or cleaner safely into the top of the vertical ear canal. Currently, veterinarians and pet owners must poor or drip a fluid directly from a bottle into the animal's ear.

This method does not allow for a measured delivery of liquid, nor is it practical since, the vast majority of dogs, cats, and other animals will resist any attempt to drop liquid medicine into their ears. This resistance makes it very difficult to get medicine or cleaner into the vertical ear canal. In fact veterinarians report that most pet owners end up getting the medicine onto the pinna 102 of the ear. When the medicine gets only onto the pinna 102 of the ear, the infection in the inner ear will typically continue unabated.

Compounding these difficulties is the fact that the inner ear is not easy to find, especially on dark haired animals. On some animals it is also not possible to get a direct line of sight into the vertical ear canal 106A without assistance. Currently, there is no means of simultaneously lighting the ear and applying a liquid. Since the current method cannot effectively get the medicine or cleaner to the vertical ear canal 104, safely, repeatedly, and without sedation of the animal, into this all-important inner ear, infections can also become worse and more resistant to medications.

Recognizing this fact, many pet owners compensate by positioning the bottle of liquid as close to or, directly up against the animal's ear before dispensing the liquid. However, the animal will typically respond to this treatment by jerking its head around, risking injury to the ear of the animal when the hard surface of the medicine bottle contacts the ear.

Such contact with tender surface of the ear of the animal can make the animal even less willing to submit to further treatments.

The present invention also improves upon existing methods for hand feeding. Current feeding syringes are made of hard and rigid materials which can injure the soft tissues of a nursing animal. Existing feeding syringes also do not take into account the variable size and shape of animal mouths, nor do they allow for safe movement of the animal during feeding.

What is needed is a system and method for safely dispensing liquids such as medicines to orifices of animals and human beings. The present invention satisfies that need.

SUMMARY OF THE INVENTION

To address the requirements described above, the present invention discloses a method and apparatus for delivering liquid within an orifice of an animal. In an exemplary embodiment, the apparatus comprises a hollow syringe defining a vessel having an open end; a plunger, slidingly and sealingly disposed within the vessel; and a flexible delivery tube, having a first end sealingly coupled to the open end and a delivery end for dispensing the liquid proximate the orifice. In another exemplary embodiment, the method comprises filling a vessel defined by a hollow syringe having an open end with the liquid; placing a delivery end of a flexible delivery tube having a first end sealingly coupled to the vessel open end proximate the orifice of the subject; and dispensing the liquid proximate the orifice of the subject by depressing a plunger disposed within the hollow syringe.

The present invention assists veterinarians and pet owners in the application of medicine and/or cleaners into or around the vertical ear canal specifically, and generally to the mouth and nose of domesticated animals. The invention is easy to use, and completely safe if used properly. The invention comprises varying sizes of syringes, depending on the volume of medicine or cleaner to be applied. Attached to the syringe is a very soft flexible medical grade silicon tube, designed to safely administer any liquid solution into the ear. The aforementioned tube may be removable/replaceable or permanently affixed to the associated syringe. Optionally, a flashlight may be attached to or integrated with the apparatus to help the user guide the silicon tube into the target area of a given orifice. Importantly, the tool can be used with one hand, freeing the other hand to restrain or calm the animal.

BRIEF DESCRIPTION OF THE DRAWINGS

Referring now to the drawings in which like reference numbers represent corresponding parts throughout.

DETAILED DESCRIPTION OF PREFERRED EMBODIMENTS

In the following description, reference is made to the accompanying drawings which form a part hereof, and which is shown, by way of illustration, several embodiments of the present invention. It is understood that other embodiments may be utilized and structural changes may be made without departing from the scope of the present invention.

Figure 1:
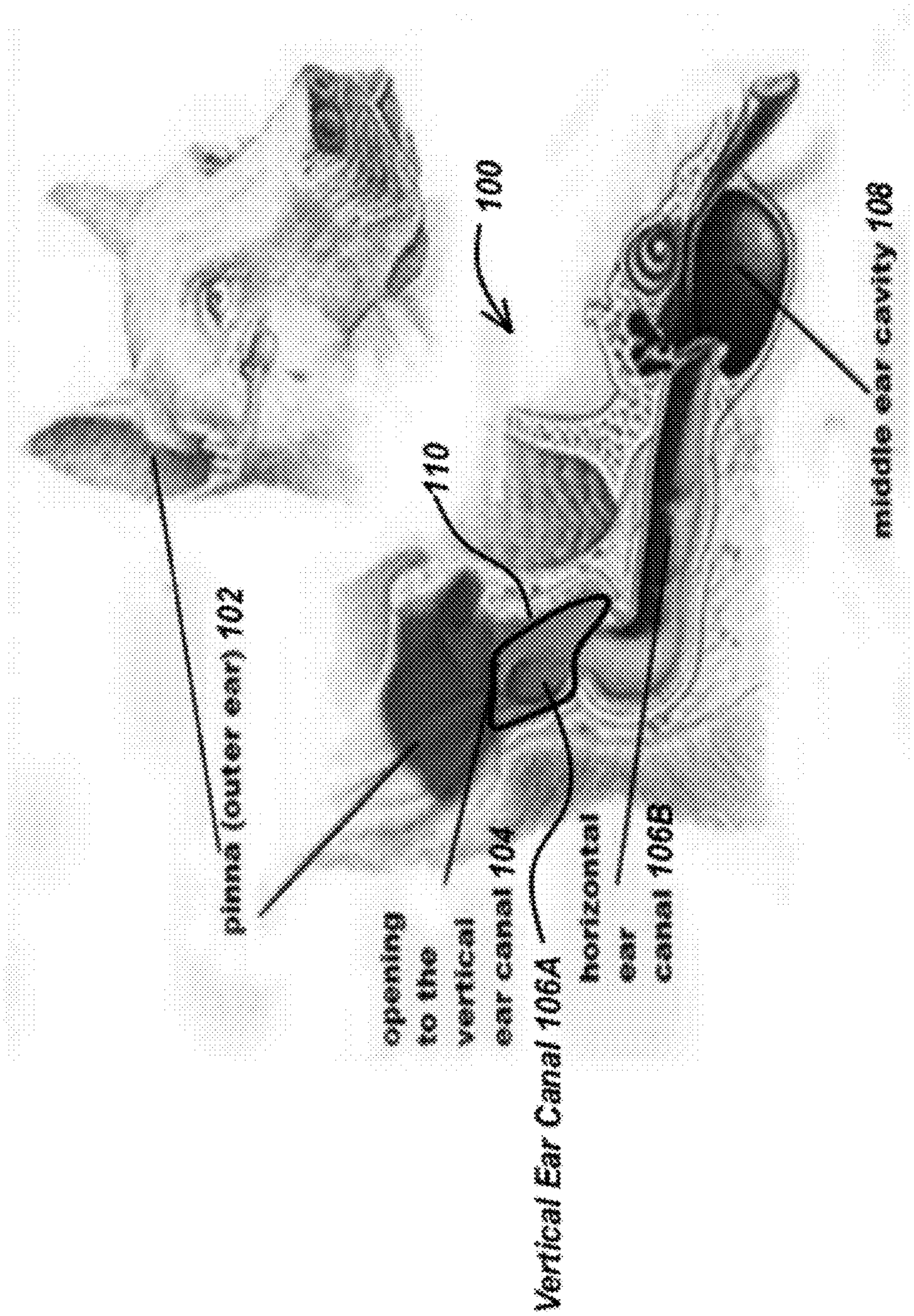
FIG. 1 is a diagram showing the ear canal and related structures of a canine.
Figure 2:
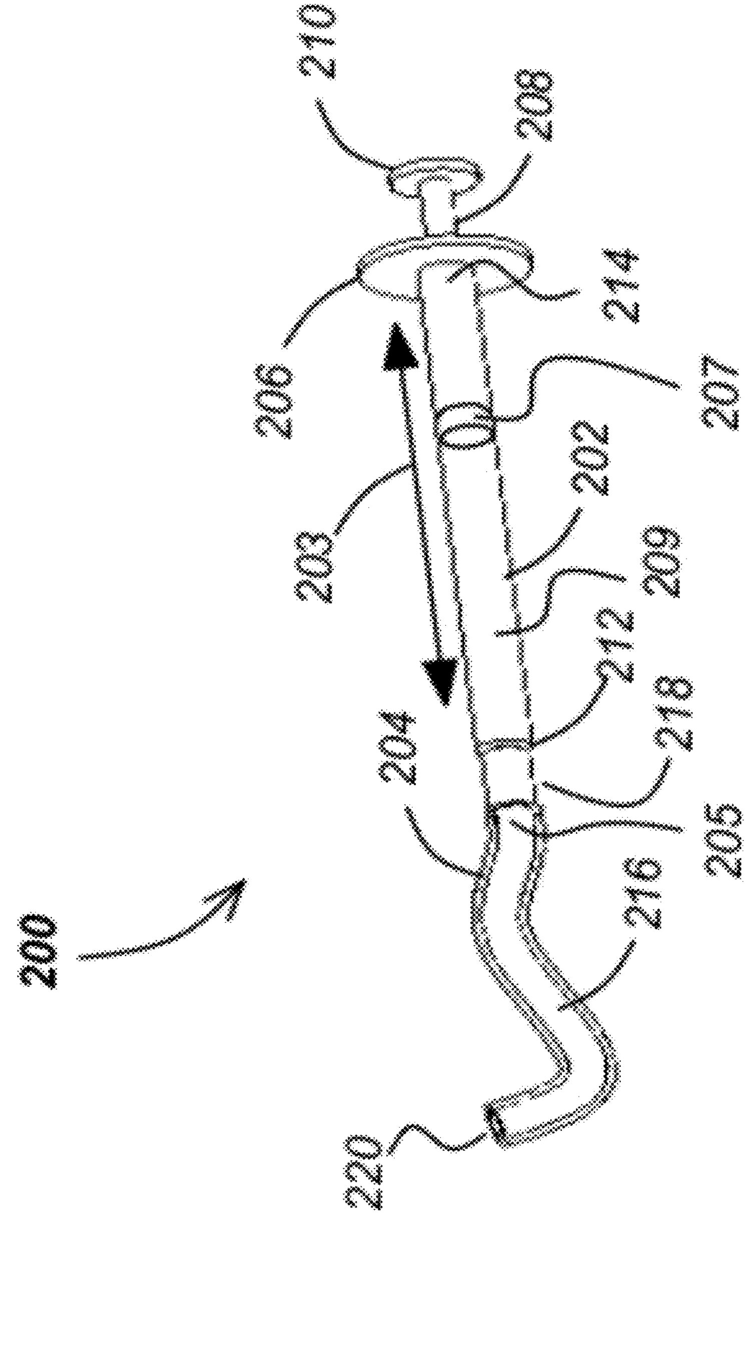
FIG. 2 is a diagram showing one embodiment of the medical tool.

FIG. 2 is a diagram showing one embodiment of the medical tool 200. The tool 200 comprises a hollow syringe 202, extending longitudinally along an axis 203. The hollow syringe 202 includes an open end 205 having a syringe body fitting 212 and a second end 214 distal from the open end 205. The medical tool also comprises a plunger 207, slidingly and sealingly disposed within the hollow syringe 202, thereby defining a vessel 209 therein.

The tool also comprises a flexible delivery tube 204. The flexible tube 204 has a first end 218 sealingly coupled to the open end of the hollow syringe 202 and a distally disposed delivery end 220 for dispensing the liquid in the vessel 209. The aforementioned "liquid" includes, but is not limited to cleaning solutions, anti-fungal solutions, and/or anti-bacterial solutions The flexible delivery tube also includes an inner portion 216 in fluid communication with the vessel 209. In one embodiment, the flexible delivery tube 204 first end first end is configured to be sealingly and removably affixed to a syringe body fitting 212 near the open end 208 of the hollow syringe 202, thereby providing fluid communication between the inner portion 216 of the flexible delivery tube 204 vessel 209. An end cap can be inserted over the delivery end 220 of the flexible delivery tube 204 if desired to prevent the escape of liquid and to enhance sterility of the liquid as well.

Figure 3:
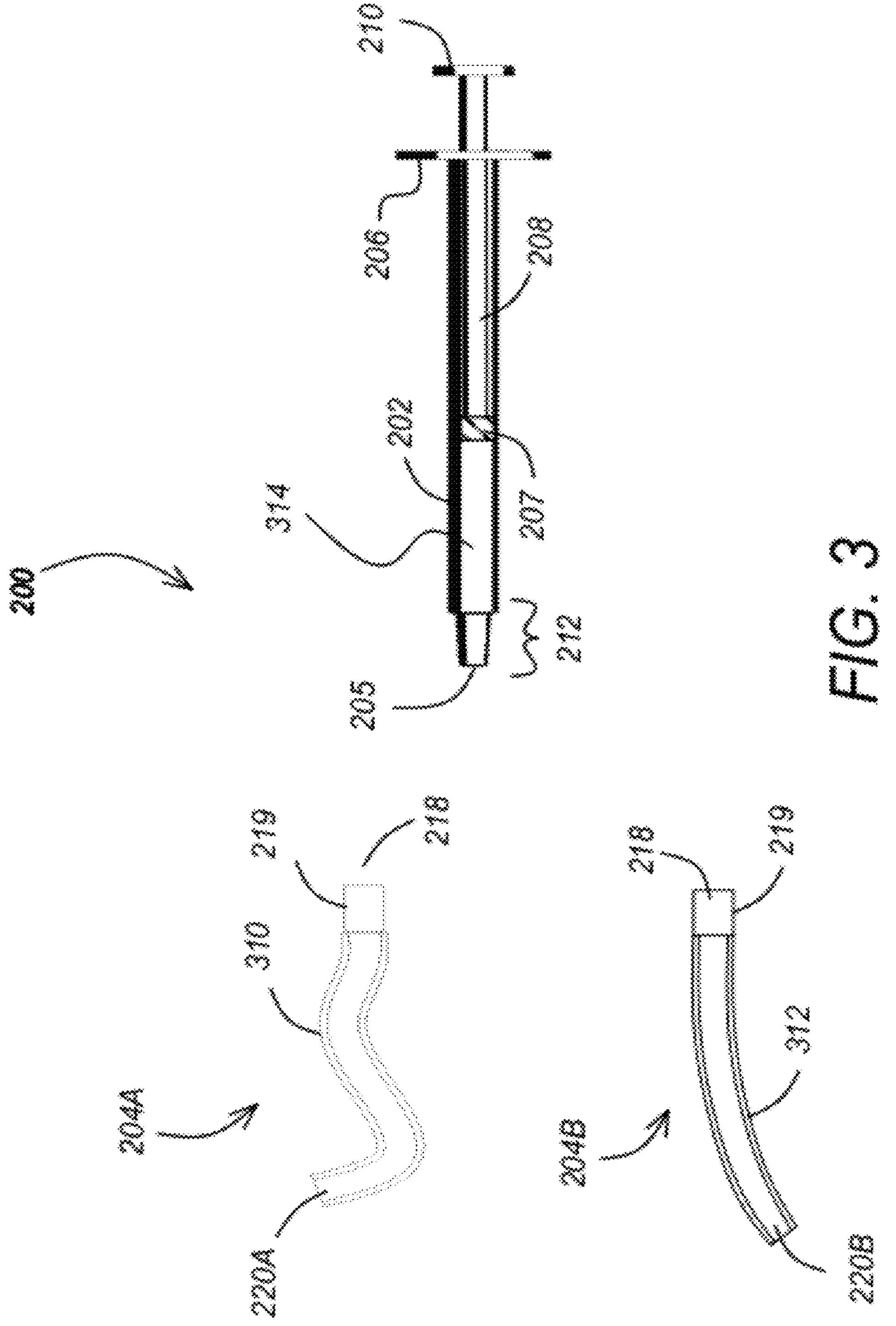
FIG. 3 is a diagram showing another view of the medical tool.

FIG. 3 is another diagram showing another view of the tool 200 shown in FIG. 2. The tool 200 includes a plunger 207 disposed in the inner portion of the hollow syringe 202. The plunger 207 provides a fluid seal with the inner surfaces of the syringe body 202, and is sealingly slidable within the syringe body 202 along axis 203 to dispense the liquid in the vessel 209 or draw liquid into the vessel 209 for later dispensing. The plunger 207 is coupled to a rod 208 having a tab 210 that allows the user to push and pull the plunger 207 within the hollow syringe 202. Force applied to the liquid by the plunger 207 pushes the liquid down through the syringe body 202 and into the flexible delivery tube 204, through and out of the flexible delivery tube 204 and to the desired location.

The capacity of the tubular syringe body 202 depends upon the application, and may vary between 0.0001 ml and 100 ml. In one embodiment, the tubular syringe body is sized to accept precisely the proper recommended doses to apply to the animal, thereby obviating the need for the pet owner to measure the liquid. To this end, specialized syringe scales may be used, which demark units of "drops" (approximately 0.3 cc). This is advantageous since most ear medicines are prescribed in units of "drops."

The characteristics of the delivery tube (length, shape, diameter, thickness, flexibility and material composition) also depend on the particular application (type of liquid to be dispensed, type and breed of animal, and orifice into which liquid is to be dispensed). For example, the optimal parameters of a flexible delivery tube 204 suitable for a large dog will typically differ from that of a small dog, and both will typically differ from that of a housecat. Different parameters can also be selected according to the breed of dog as well.

In one embodiment, the length of the delivery tube 204 varies between 1 mm for a very small animal such as a mouse, and 100 cm for a large animal such as a horse), the width of the delivery tube between 1 micron for very small animals and as much and 1 centimeter for large animals. Preferably, the flexible tube 204 is fashioned of medical grade silicone tubing of appropriate thickness to assure that it does not kink, yet can be inserted an adequate distance into the animal's orifice without injury. The flexible delivery tube 204 is also soft and pliable enough to ensure that the animals' ear cannot become injured during the proper use of the tool. For dispensing liquid into a dog's ear, the preferred delivery tube characteristics include, for example, an inner diameter of 0.062 inches, an outer diameter of 0.125 inches, and a length of about 2 inches, and is fashioned of medical grade silicone tubing.

If the liquid must be inserted into the ear canal 106 of the animal directly, the flexible delivery tube 204 can be sized and shaped so as to permit insertion of the deliver end 220 of the flexible tube 204 through the opening to the ear canal 104 and within the ear canal 106 itself (preferably in the upper (vertical) portion 106A of the ear canal). The flexible tube 204 can also be shaped so that when at rest and un-flexed, it assumes a shape approximating that of the area of the animal's ear that the flexible tube 204 will be inserted into. This could include, for example the external structures (i.e. the pinna 102) proximate the orifice.

The syringe body 202 can accept one of a set of flexible delivery tubes 204 of different shapes and sizes and constructed of different materials. Given this set of flexible delivery tubes 204, the user can select the appropriate flexible delivery tube 204 according to the needs of the subject. For example, FIG. 3 illustrates two different flexible tubes 204A, 204B. When un-flexed, flexible tube 204A has the shape of a question mark, while flexible tube 204B has a curvilinear shape. Both shapes not only facilitate delivery of the liquid by more closely accommodating the shape of the pinna 102, opening of the ear canal 106 and perhaps, the ear canal itself, the shape also allows better illumination of the area to which the liquid is being dispensed, as will be made clear as the other embodiments are discussed below.

FIG. 3 also further illustrates exemplary structures that allow the flexible tube 204 to be removably and sealingly affixable to the syringe body 202. These structures include a tapered slip-fit syringe body fitting 212 at the delivery end 306 of the syringe body 202 and an attachment structure 219 at the first end 218 of the flexible tube 204 opposing the delivery end 220 of the flexible delivery tube 204. The inner diameter of the attachment structure 219 is selected such that it can be sealingly pressed over the body fitting 212. The body fitting 212 may comprise one or more ridges to grip the flexible tube 204 to assure that it stays attached to the syringe body 202 when in use, while permitting the flexible tube 204 to be removed. The body fitting or flexible delivery tube may have an inner coating of silicone and/or Teflon to improve seal and ease of use. A suitable body fitting is currently available at www.coleparmer.com. The flexible tube 204 may also be permanently attached to the syringe body 202, if desired, and sold together as an integrated unit.

Animal ears include complex structures that are unfamiliar to the vast majority of pet owners. Animal ears are also typically lined with a substantial amount of hair, often substantially obscuring the structures of the ear from view. Upon smelling medicine, animals will often attempt to run to the darkest place that they can find, then begin moving and shaking their head. Consequently, it is difficult for a pet owner to find the opening to the ear canal 104. While it is possible for the pet owner to obtain a flashlight to assist in the process, it is unusually difficult for a single pet owner to simultaneously calm a pet, hold a light, and dispense medication at the same time. Even if another person is available to hold or calm the pet, the mere presence of two people instead of one can make it difficult to calm the pet.

Figure 4:
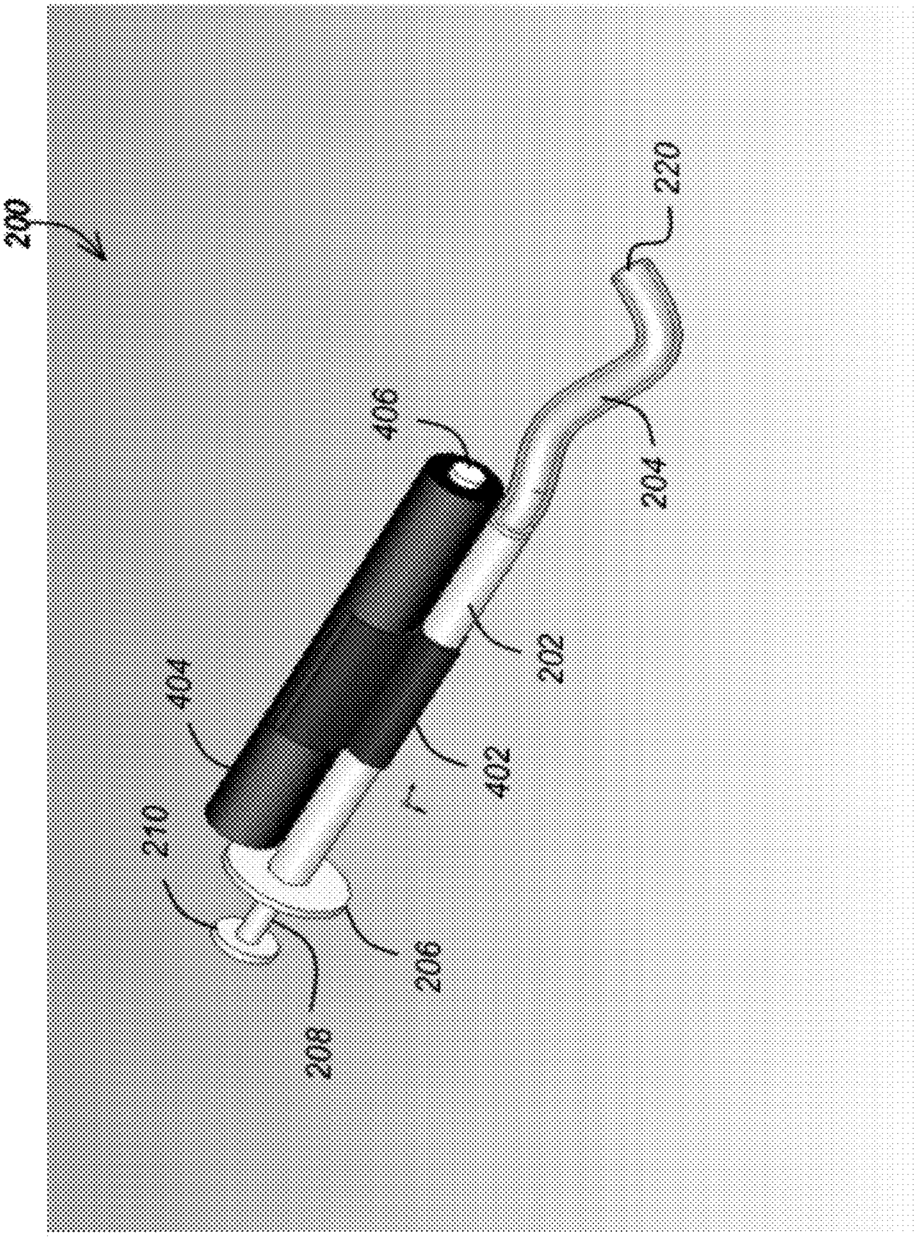
FIG. 4 is a diagram illustrating an embodiment in which the medical tool includes a light source.

FIG. 4 is a diagram illustrating an embodiment in which the medical tool 200 includes a light source 406 to assist the user in finding the opening to the ear canal 104. In the illustrated embodiment, the medical tool includes an attached flashlight 404 having a light source 406 directed to the vicinity of the dispensing end 220 of the flexible delivery tube 204. The flashlight 404 may be powered by battery, solar energy, or by a remote DC or AC source. Further, the light source 406 can comprise an incandescent bulb, a light emitting diode (LED), a fluorescent light, or any other light source.

In the illustrated embodiment, the flashlight 404 is attachable and detachable via a clip 402 attached around the periphery of the hollow syringe 202 and the flashlight 404. The dimensions of the clip 402 depend on the diameter of the syringe body 202 and flashlight 404, but in one embodiment, the clip is sized to securely hold a "MAGLIGHT" such as a "MINI MAGLIGHT." The clip 402 is preferably fashioned out of plastic, but may be fashioned from any suitable material, including rubber or spring metal.

The flashlight 406 can also emit light energy in different wavelengths to assist the user in finding the opening of the ear canal 104. For example, since the inner structures of the ear are often pink in color, the light emanating from the light source 406 can be selected in shorter (bluish) wavelengths to maximize contrast. The light source 406 may also be selected to include some UV or infrared wavelengths, and can be matched with the medication to assist in the dispensing of the medication within the ear canal 106. For example, pigment may be added to the medication that glows when exposed to light of the proper wavelength, much like a blacklight. This allows the pet owner to visually determine if the medication is being dispensed where required.

Figure 5:
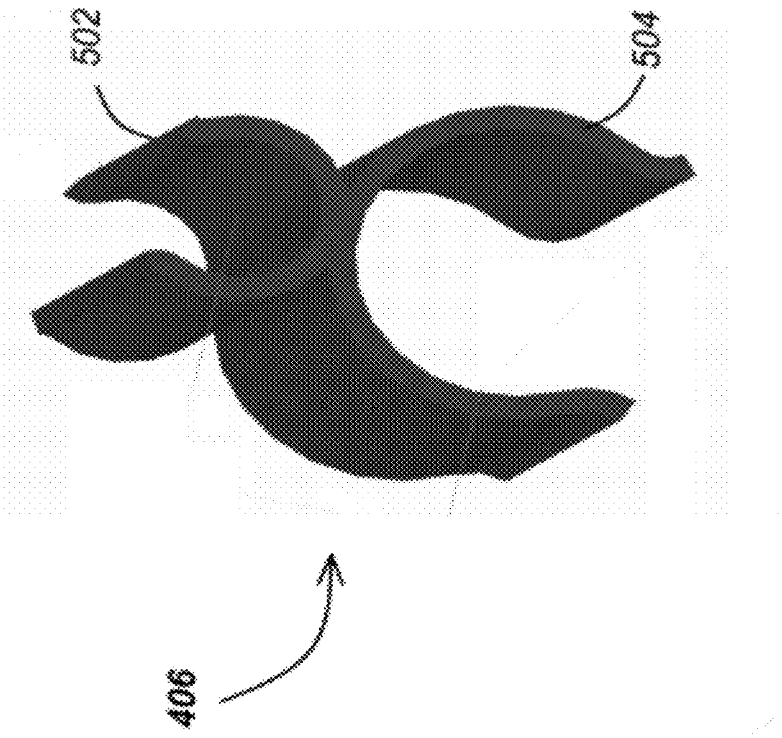
FIG. 5 is a diagram showing one embodiment of a clip.

FIG. 5 is a diagram showing one embodiment of the clip 406. In this embodiment, the clip 406 comprises a first portion 504 sized and shaped to clip around and securely hold the syringe body 202 and a second portion 502 attached to the first portion 504 that is sized and shaped to clip around and securely hold the flashlight 406.

Although the embodiment shown in FIG. 4 illustrates an embodiment wherein a flashlight 404 is coupled to the outer periphery of the medical tool 200 via a plastic clip, the flashlight 404 can be permanently attached to the outer periphery of the syringe body 202 or may be removably attached by other means. For example, the flashlight 406 may be attached to the syringe body 202 via a strap of hook and loop fasteners such as VELCRO, or a combination of a clip 402 and strap, with the clip sized to attach to the syringe body 202 and the strap expandable to accommodate a wide variety of sizes and shapes of flashlights 406.

Figure 6:
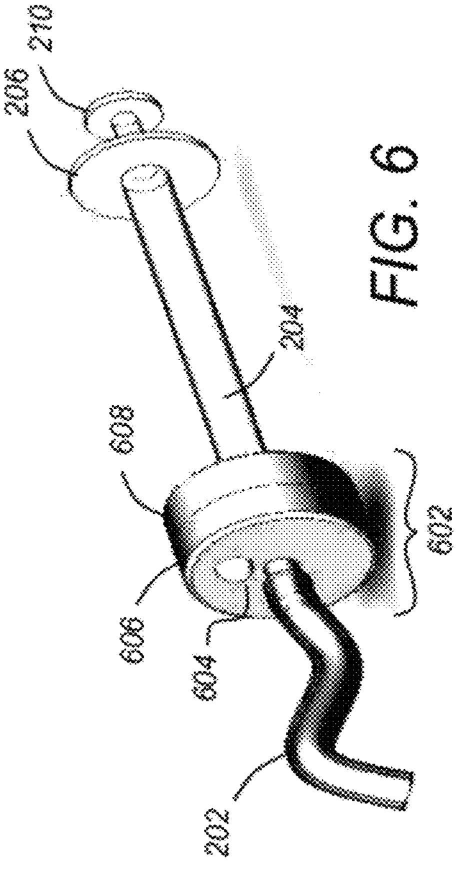
FIG. 6 is a diagram of another embodiment of the medical tool.
Figure 8:
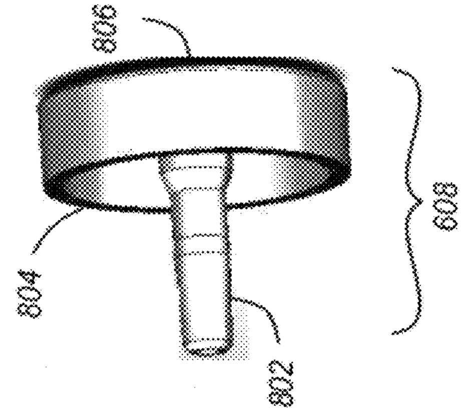
FIGS. 7 and 8 are diagrams showing perspective views of an embodiment of the light module.
Figure 7:
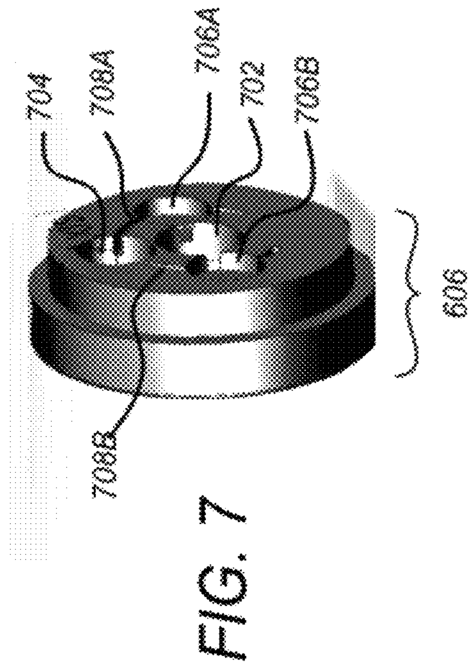

FIG. 6 is another embodiment of the medical tool 200. In this embodiment, the light source 604 is integrated with a light module 602 that is itself integrated with the medical tool 200 by placement between the syringe body 202 and the flexible tube 202. In the illustrated embodiment, the light module 602 includes a first housing 606 and a second housing 608. FIGS. 7 and 8 are perspective views of one embodiment of the first housing 606 and the second housing 608. In the illustrated embodiment, the second housing 608 comprises a conduit 802 which, when assembled with the first housing 606 passes through the light module 602 to provide fluid communication between the syringe body 202 and the flexible tube 202. The second housing 608 and the first housing 606 are assembled to create the light module 602 by passing the conduit 802 through an aperture 702 in the first housing 606. The syringe body fitting 212 fits into the open end 806 of the second housing 608, sealingly placing the conduit 802 in fluid communication with the interior of the syringe body 202. The interior surface of the conduit 802 in this area may include, for example, a plastic substance similar or identical to the material used in the flexible tube 204 to assure that the conduit is sealed to the syringe body fitting 212.

The first housing 606 also includes a further aperture 704. The light source 604 can be inserted into this aperture, with the light emitting portion facing away from the face shown in FIG. 7. Electrical leads from the light source 604 may be bent to pass through channels 708A and 708B, which extend to first 706A and second 706B depressions, each sized and shaped to accept a battery therein. The electrical leads make contact with batteries placed in the depressions 708, thus establishing at least a portion of an electrical circuit that provides power to the light. The circuit can be completed (allowing power to pass to the light source 604) by electrical contacts within the second housing 608 that are made when the second housing 608 is rotated relative to the first housing 606 and broken when the rotation is reversed or continued.

The first and second housings 606, 608 as well as the interface between the light source 604 and the aperture 702 may include gaskets or other sealants as necessary so that the lighting module 602 can be immersed in water or other solvents to clean the medical tool 200.

In an alternate embodiment of the light module 602, the aperture 702 is sufficiently widened to permit passage of the flexible delivery tube 204 there through, so that the delivery tube 204 can be connected directly to the syringe body fitting 212. This requires longer flexible delivery tubes, and for the outer diameter of the delivery tube to be properly matched to the diameter of the aperture so that the light module 602 remains in place, but this embodiment allows the user to affix a soft syringe tip directly to the tip of the syringe, as opposed to the soft syringe tip being affixed to the conduit 802. Light module 602 may also be integrated with larger multi-dose syringe. In this embodiment, the light module 602 may be either attachable/detachable, or permanently affixed to a multi-dose syringe.

Figure 9:
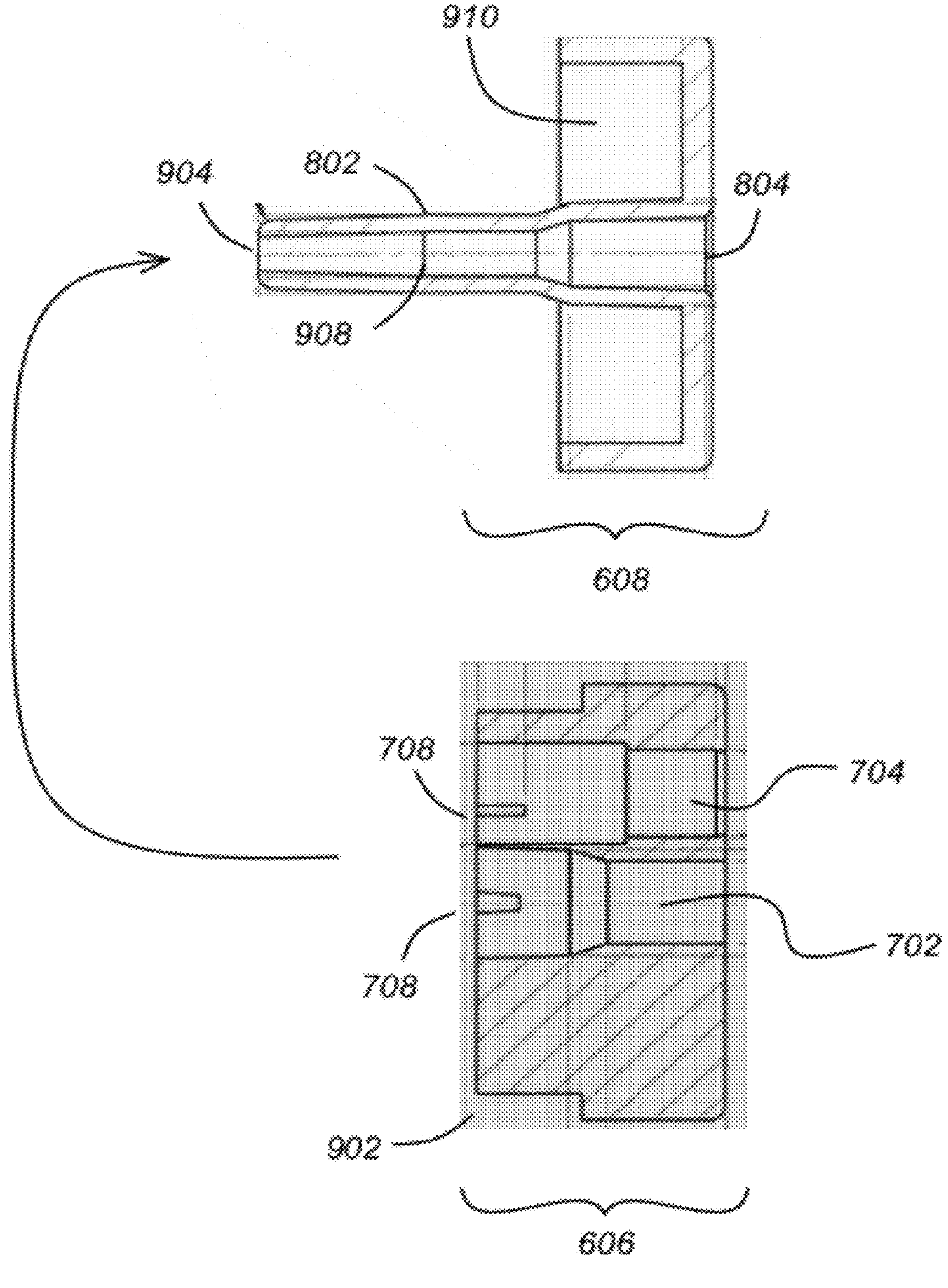
FIG. 9 is a diagram showing a cross sectional view of one embodiment of the light module.

FIG. 9 is another diagram of the first housing 606 and the second housing 608, showing the internal structures of both. The conduit 802 of the second housing 608 includes an interior portion 908 through which the liquid travels when being passed from the syringe body 202 to the flexible tube 204. A length of the conduit's outer surface distal from the opening 804 can be tapered in the same way as the syringe body fitting 212 to permit attachment of the flexible tube to the conduit 802. Further, other portions of the conduit may be shaped to interface with complimentary structures in the aperture 702 of the first housing 606 to permit secure attachment of the first housing 606 to the second housing 608. FIG. 9 also illustrates channels 708A and 708B, and the internal shape of aperture 704, which permits insertion of the light source 604, and also illustrates the shelf structure 902 of the first housing 606 which permits the first housing to be inserted into the concave area 910 formed by the second housing 608.

Also, although shown as separate and disconnectable items, the syringe body 202, flexible delivery tube 204, and light source 604 may comprise an integrated structure with all three or a subset of these elements. The light source 604 may also be integrated with or placed adjacent the first end 218 of the fluid delivery tube so that light travels within the flexible fluid delivery tube toward its dispensing end 220B.

Figure 10A:
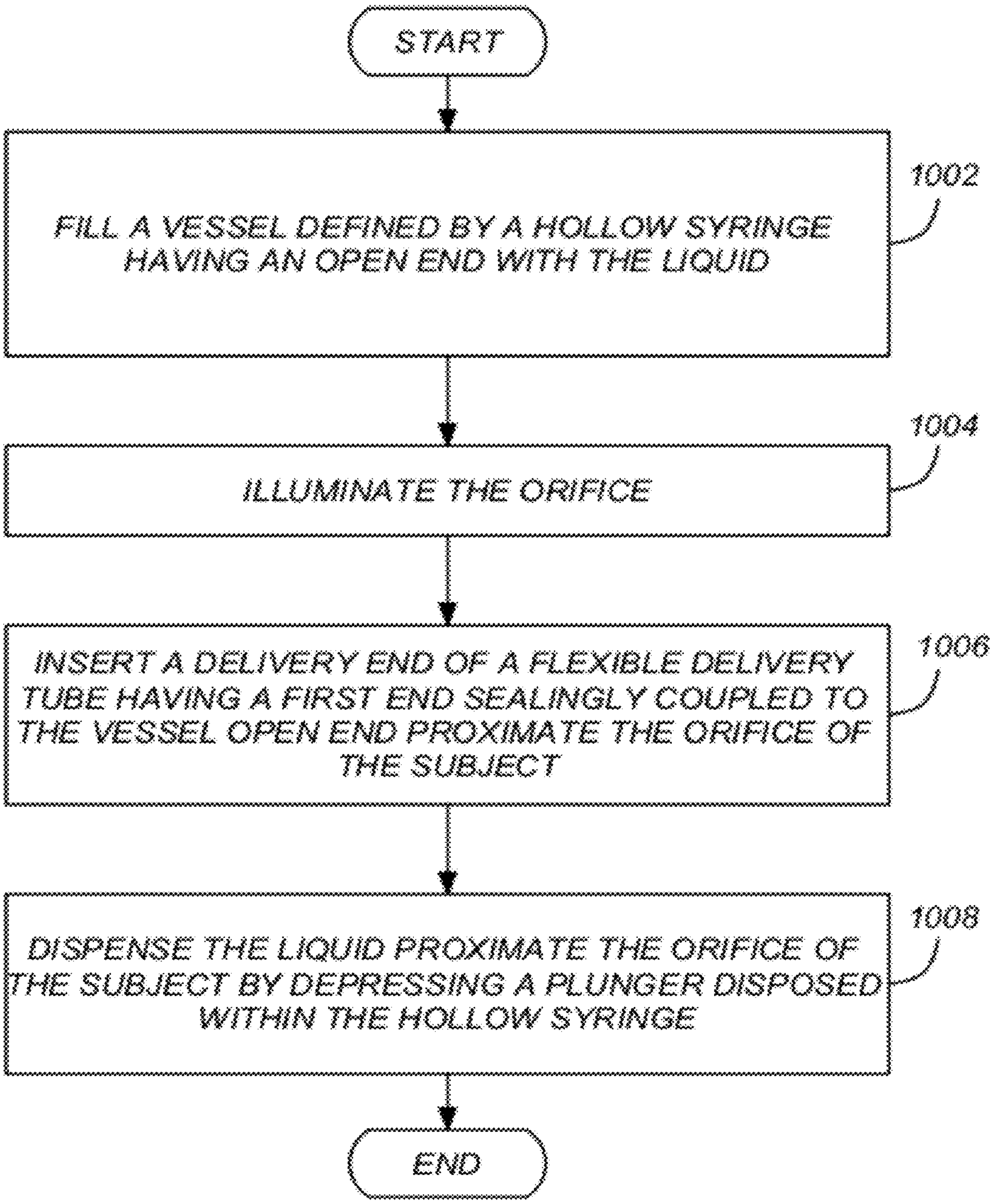
FIGS. 10A and 10B are diagrams showing exemplary method steps that can be used to practice one embodiment of the present invention.
Figure 10B:
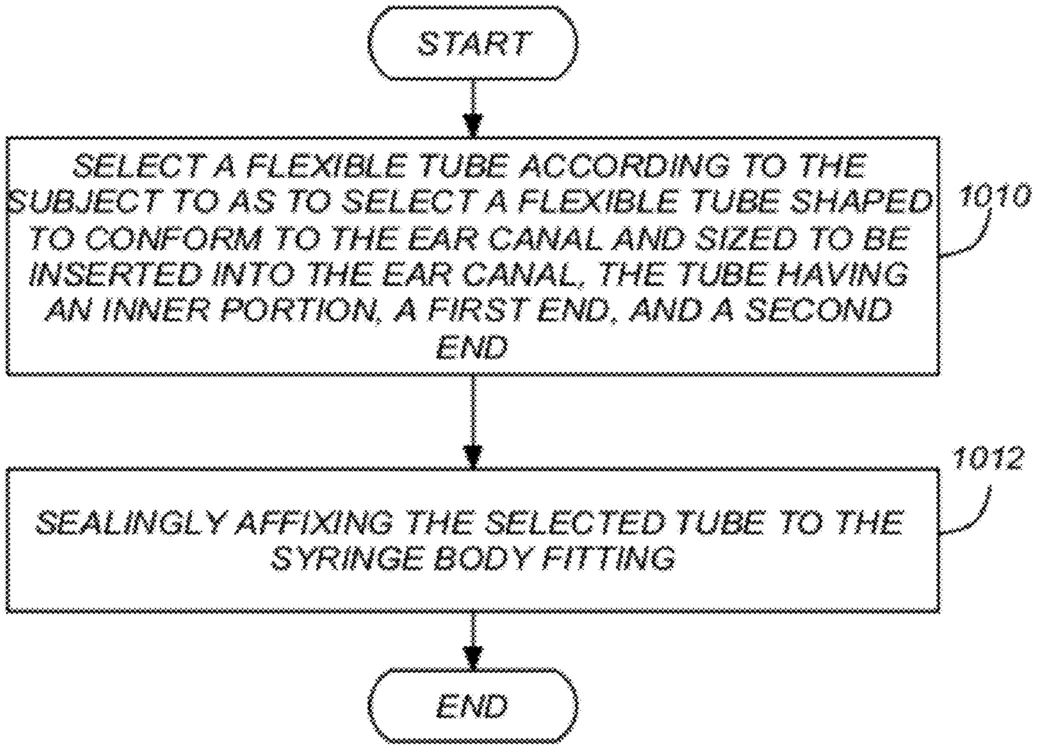

FIGS. 10A and 10 are flowcharts illustrating exemplary techniques for delivering liquid within an orifice 104 or other orifice of an subject. A shown in block 1002, a vessel 209 defined by a hollow syringe 202 having an open end 205 is filled with the liquid (such as a medication or cleaning solution). This can be accomplished by placing the syringe body fitting 202 in a container of the liquid, and pulling back on the plunger 207 via the rod 208 to draw the liquid into the vessel 209 of the hollow syringe 202. The flexible delivery tube 204 can then be placed on the syringe body fitting 202 to prepare the medical tool 200 for use. Alternatively, the flexible delivery tube 202 may be attached to the syringe body 202 when the liquid is drawn, thus drawing the liquid through the flexible delivery tube 202 and the opening 205 and into the vessel 209. The liquid may also be inserted into the vessel 209 by filling from the second end 214 of the hollow syringe 202, with the plunger 207 removed, then inserting the plunger 207 into the syringe body 202.

As shown in block 1004, opening 104 can be illuminated by the optional light source 604. The delivery end 220 of the flexible delivery tube 204 is then placed proximate the desired orifice (e.g. ear canal opening 104) of the subject, as shown in block 1006, and the liquid is dispensed within the ear canal of the subject by depressing a plunger 207 sealingly slidable within the hollow syringe 202 via a rod 208 coupled to the plunger 207. If desired, the delivery end 220 of the flexible delivery tube 204 can be inserted through the orifice 104 and into the ear canal 106 of the subject before the liquid is dispensed.

As described above, the medical tool 200 may be provided with a set of replaceable flexible delivery tubes 204, each delivery tube 204 being intended for use with different subjects and/or orifices of varying physical characteristics. For example, a flexible tube 204 may be provided that has suitable characteristics for insertion into the ear canal 106 of a large dog, while a different flexible tube 204 is suitable for the ear canal 106 of a different animal, such as a small dog, a cat, or a horse. The pet owner selects the appropriate flexible delivery tube 204 according to the subject so that the selected flexible tube 202 has the appropriate characteristics (e.g. diameter, length, material thickness, shape, and flexibility) to be inserted into the orifice of interest of the subject. After the appropriate replaceable flexible tube 204 is selected, it is affixed to the syringe body fitting 216. This is shown in blocks 1010 and 1012 of FIG. 10B.

The aforementioned medical tool 200 as a whole may to be fully immersed in a suitable cleaning/disinfecting/sanitizing solution such as alcohol, hydrogen peroxide, and/or water, and is designed to minimize surfaces that can accumulate material from inside the animal's ear. Similarly, if the batteries are removed, the medical tool 200 can be sterilized in an autoclave.

The veterinary profession as a whole has and continues to prescribe to its patients thick creams and/or thick liquid solutions for the treatment of inner ear infections. The medical tool 200 allows such solutions to be placed further within the animal's ear than current methods. However, in cases where these solutions are too thick to be effectively used in the tool 200, they are also too thick to effectively work their way down into the vertical ear canal 106A of the animal. In such cases, the thick solution can be watered down with a neutral liquid such as saline. Using this watering method, the thick solutions become simultaneously capable of being dispensed from a syringe and also working their way down into the vertical ear canal.

Conclusion

This concludes the description of the preferred embodiments of the present invention. The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. An apparatus for delivering liquid proximate an orifice of a subject, comprising:
- a hollow syringe defining a vessel having an open end;
- a plunger, slidingly and sealingly disposed within the vessel;
- a flexible delivery tube, having a first end sealingly coupled to the open end and a delivery end for dispensing the liquid proximate an orifice of a subject; and
- a light module having:
  - a light source;
  - a first housing, having a conduit passing through the light module, the conduit for providing fluid communication between the syringe body and the flexible tube;
  - a second housing, releasably affixable to the first housing, the second housing having
    - a first aperture providing a passage for the conduit when the second housing is affixed to the first housing; and
    - a second aperture, having the light source placed therein.

2. The apparatus of claim 1, wherein the delivery end is for dispensing liquid within the orifice of the subject.

3. The apparatus of claim 2, wherein the orifice is an ear canal, and the delivery end of the flexible delivery tube is sized for insertion into the ear canal of the subject.

4. The apparatus of claim 2, wherein the light source illuminates an area proximate the delivery end of the flexible delivery tube.

5. The apparatus of claim 4, wherein the light module is removably affixed to the syringe via a clip removably affixable to the syringe.

6. The apparatus of claim 4, wherein the area illuminated by the light source is offset from an axis of the hollow syringe, and the flexible delivery tube is shaped so that the delivery end of the flexible delivery tube is illuminated by the light source.

7. The apparatus of claim 6, wherein the flexible delivery tube is question mark shaped.

8. The apparatus of claim 1, wherein the flexible delivery tube is comprised of medical grade silicone tubing.

9. The apparatus of claim 1, wherein the open end of the vessel comprises a syringe body fitting, configured to accept and sealingly affix the first end of the flexible delivery tube.

10. The apparatus of claim 1, wherein the flexible delivery tube and the hollow syringe are an integrated assembly.

11. The apparatus of claim 1, wherein the flexible delivery tube and the syringe are decoupleable.

12. The apparatus of claim 1, wherein the flexible delivery tube is 0.062 inches in inner diameter, 0.125 inches in outer diameter, and two inches long.

13. A method of delivering liquid within an orifice of a subject, comprising the steps of:

filling a vessel defined by a hollow syringe having an open end with the liquid;

illuminating an orifice of a subject with a light module attached to the vessel, the light module having:

a light source:

a first housing, having a conduit passing through the light module, the conduit for providing fluid communication between the syringe body and the flexible delivery tube; and a second housing, releasably affixable to the first housing, the second housing having a first aperture providing a passage for the conduit when the second housing is affixed to the first housing; and a second aperture, having the light source placed therein;

placing a delivery end of the flexible delivery tube having a first end sealingly coupled to the vessel open end proximate to the orifice of the subject;

dispensing the liquid proximate the orifice of the subject by depressing a plunger disposed within the hollow syringe.

14. The method of claim 13, wherein the orifice is an opening to an ear canal of an animal.

15. The method of claim 13, wherein the light source is disposed between the hollow syringe and the flexible delivery tube.

16. The method of claim 13, further comprising the step of:

inserting the delivery end of the flexible delivery tube through the orifice of the subject before dispensing the liquid.

17. The method of claim 16, wherein the flexible tube is removably attachable to the syringe open end, and the method further comprises the steps of:

selecting a flexible tube from a set of flexible delivery tubes according to the subject to select the proper shape and size of flexible tube for the subject and orifice.

* * * * *